United States Patent [19]

Berg

[11] 4,363,704

[45] Dec. 14, 1982

[54] SEPARATION OF TOLUENE FROM NON-AROMATIC HYDROCARBONS BY EXTRACTIVE DISTILLATION

[76] Inventor: Lloyd Berg, 1314 S. Third Ave., Bozeman, Mont. 59715

[21] Appl. No.: 323,544

[22] Filed: Nov. 20, 1981

[51] Int. Cl.³ .............................................. B01D 3/40
[52] U.S. Cl. ...................................... 203/58; 203/59; 203/60; 203/61; 203/62; 203/64; 203/65; 203/67; 585/866
[58] Field of Search ............... 585/800, 833, 856–867; 203/57, 61, 58, 59, 60, 62–65, 67

[56] References Cited

U.S. PATENT DOCUMENTS

| | | | |
|---|---|---|---|
| 2,431,655 | 11/1947 | Amos et al. | 585/866 |
| 2,655,467 | 10/1953 | Cooper et al. | 203/61 |
| 3,114,783 | 12/1963 | Butler et al. | 203/61 |

*Primary Examiner*—Frank Sever

[57] ABSTRACT

Toluene is virtually impossible to separate from similar boiling non-aromatic hydrocarbons by conventional rectification or distillation. Toluene can be readily separated from similar boiling non-aromatic hydrocarbons by using extractive distillation in which the extractive agent is a mixture of phthalic anhydride and/or maleic anhydride plus a suitable solvent. A typical mixture comprises phthalic anhydride, maleic anhydride and glycerol triacetate.

3 Claims, No Drawings

SEPARATION OF TOLUENE FROM NON-AROMATIC HYDROCARBONS BY EXTRACTIVE DISTILLATION

FIELD OF THE INVENTION

This invention relates to a method for separating toluene from close boiling non-aromatic hydrocarbons using mixtures of two or more compounds as extractive agents in extractive distillation.

DESCRIPTION OF THE PRIOR ART

Extractive distillation is the method of separating close boiling compounds by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum boiling azeotropes with them. Usually the extractive agent is introduced a few plates from the top of the column to insure that none of the extractive agent is carried over with the lowest boiling component. This usually requires that the extractive agent boil twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

The separation of toluene by extractive distillation has been reported as far back as 1945. C. L. Dunn, R. W. Millar, G. J. Pierotti, R. N. Shiras and M. Souders, Jr. in Trans. AIChE., 41, 631 (1945) reported on the effectiveness of a number of pure compounds. Their results are summarized in Table I. Their data is virtually impossible to duplicate because for the non-aromatic hydrocarbon, they used a dearomatized straight run naphtha boiling close to toluene. Since no two naphthas are exactly the same, their results serve only to indicate the relative merits of the several extractive agents. Thus they show furfural to be the most effective with a relative volatility of 2.30, then acetonylacetone at 2.20 and so on down the table. It might be recalled that in 1945, no non-aromatic hydrocarbon boiling close to toluene was available to them for experimental work.

TABLE I

Relative Volatility of Non-aromatics to Toluene for Several Pure Extractive Distillation Agents.

| Solvent | B.P, °F. | Wt. % Solvent | Volatility Ratio |
| --- | --- | --- | --- |
| Furfural | 325 | 50 | 2.30 |
| Acetonylacetone | 370 | 50 | 2.20 |
| Nitrobenzene | 412 | 50 | 2.16 |
| Nitrotoluene | 432 | 50 | 2.16 |
| Phenol | 360 | 50 | 2.10 |
| Aniline | 363 | 50 | 2.08 |

TABLE I-continued

Relative Volatility of Non-aromatics to Toluene for Several Pure Extractive Distillation Agents.

| Solvent | B.P, °F. | Wt. % Solvent | Volatility Ratio |
| --- | --- | --- | --- |
| Chlorex, (dichloro-diethyl ether) | 352 | 50 | 2.09 |
| Phenyl cellosolve | 464 | 50 | 2.01 |
| Phenol-Cresol (60-40) | 378 | 50 | 1.98 |
| Phenol-Cresol (40-60) | 383 | 50 | 1.95 |
| Acetophenone | 396 | 50 | 1.95 |
| 1-Methoxy-2-hydroxy-3-phenoxypropane | 532 | 50 | 1.92 |
| Ethyl carbitol | 396 | 50 | 1.85 |
| m-Cresol or p-Cresol | 396 | 50 | 1.85 |
| 1-Ethoxy-2,3-dihydroxypropane | 432 | 50 | 1.80 |
| 1-Isopropoxy-2,3-dihydroxypropane | 439 | 50 | 1.70 |
| Diacetone glycol | 374 | 50 | 1.64 |
| 1-Methoxy-2,3-dihydroxypropane, 20. | 428 | 50 | 1.46 |

H. L. Thompson in U.S. Pat. Nos. 3,537,984 and 3,723,256, Brit. Pat. No. 1,392,735 (Apr. 30, 1975) and Canadian Pat. No. 962,212 (Feb. 4, 1975) reported on the use of sulfolane as the extractive distillation agent in the separation of toluene from non-aromatic hydrocarbons. In German Pat. No. 2,225,994 (Dec. 13, 1973) he described the use of tetramethylene sulfone. P. Mikitinko, G. Cohen & L. Asselinieau, German Pat. No. 2,313,603 (Sept. 27, 1973) separated both benzene and toluene from non-aromatic hydrocarbons using dimethyl formamide and dimethyl acetamide. P. Mikitinko & L. Asselineau in German Pat. No. 2,809,985 (Sept. 14, 1978) used these same reagents with water added to bring the non-aromatic hydrocarbons off overhead as a two-phase azeotrope and thus lower the boiling point. K. Eisenlohr & H. Mueller in German Pat. No. 2,263,344 (Dec. 23, 1972) reported on an improved equipment arrangement to separate both benzene and toluene from non-aromatic hydrocarbons by extractive distillation. G. Preusser, M. Schulze, K. Richter & W. Heuwels in German Pat. No. 1,960,857 (Dec. 4, 1969) described the use of morpholine and some of its derivatives for this separation. Improved equipment for this separation was presented by E. Mueller & K. P. John in German Pat. No. 1,808,758 (Nov. 14, 1968). It should be noted that all the work reported to date deals with the use of a single compound as the extractive distillation agent.

The advantage of using extractive distillation in this separation can be seen from Table II below.

TABLE II

Theoretical Plates Required vs. Relative Volatility for Toluene-Methylcyclohexane Separation, 99% Purity.

| Relative Volatility | Theoretical Plates Required at Total Reflux, 99% Purity |
| --- | --- |
| 1.50 | 227 |
| 1.60 | 195 |
| 1.70 | 173 |
| 2.00 | 133 |
| 2.50 | 100 |
| 3.00 | 84 |
| 3.50 | 73 |
| 4.00 | 66 |
| 4.50 | 61 |
| 5.00 | 57 |
| 5.50 | 54 |

The relative volatility of toluene to methylcyclohexane is 1.50. To separate these two in 99% purity by conventional rectification requires a minimum of 227 theoretical plates. With an extractive distillation agent such as furfural, (Dunn's best) having a relative volatility of about 3.35, it is 76. With Thompson's best, sulfolane, relative volatility of about 2.15, it is 120, and with Mikitinko's best, dimethyl formamide, relative volatility of about 3.60, it is 72. The best extractive distillation agents that I have discovered push the relative volatility as high as 4.9 and Table II shows that they will reduce the theoretical plate requirement to 48 plates.

Extractive distillation typically requires the addition of an equal amount to twice as much extractive agent as close boiling compounds on each plate in the rectification column. The extractive distillation agent should be heated to about the same temperature as the plate into which it is introduced. Thus extractive distillation imposes an additional heat requirement on the column as well as somewhat larger plates for the same product output. To be economically attractive, the extractive distillation system must save more in the reduction of the number of theoretical plates and the size of the column than it adds in the cost of larger plates and additional heat requirement. This will vary depending on the difficulty of the separation and the cost of heat. I found that in the separation of toluene from methylcyclohexane, the extractive agent should increase the relative volatility to about 3.75 to make the process economically attractive under the equipment and heat costs in effect at the time of my investigation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. I recommend twenty Centigrade degrees or more difference.

TABLE III

Relative Volatilities of Toluene to Methylcyclohexane, 2,4,4-Tri methylpentene-1 and 2,2,4-Trimethylpentane with Several Extractive Distillation Agents.

| Extractive Distillation Agent | MecycloHex-Toluene | 244TMP-1 Toluene | 224TMP Toluene |
|---|---|---|---|
| Ph.anh, Mal. anh, Glycerol triacetate | 4.25 | 3.45 | 5.18 |
| Ph.anh, Glyceroltriacetate | 3.20 | 3.43 | 4.03 |
| Mal.anh, Glyceroltriacetate | 3.10 | 3.70 | 4.14 |
| Glycerol triacetate | 2.85 | 2.79 | 3.01 |
| Ph.anh, Mal.anh, Dimethylformamide | 4.04 | 3.81 | 5.20 |
| Ph.anh, Dimethylformamide | 3.76 | 3.60 | 4.50 |
| Mal.anh, Dimethylformamide | 4.65 | 3.41 | 4.82 |
| Dimethylformamide | 3.60 | 3.73 | 3.90 |
| Ph.anh, Mal.anh, Ethylene glycol phenyl ether | 4.00 | 3.45 | 4.39 |
| Ph.anh, Ethylene glycol phenyl ether | 3.35 | 3.07 | 3.72 |
| Mal.anh, Ethylene glycol phenyl ether | 3.00 | 3.68 | 4.00 |
| Ethylene glycol phenyl ether | 2.80 | 2.90 | 3.69 |
| Ph.anh, Mal.anh, Dichlorodiethyl ether | 4.10 | 3.48 | 3.96 |
| Ph.anh, Dichlorodiethyl ether | 3.30 | 2.95 | 3.85 |
| Mal.anh, Dichlorodiethylether | 3.15 | 3.00 | 3.56 |
| Dichlorodiethyl ether | 2.70 | 2.05 | 3.50 |
| Ph.anh, Mal.anh, Ethylene glycol diacetate | 3.91 | 3.30 | 3.94 |
| Ph.anh, Ethylene glycol diacetate | 3.10 | 3.60 | 4.15 |
| Mal.anh, Ethylene glycol diacetate | 3.63 | 3.35 | 4.26 |
| Ethylene glycol diacetate | 3.10 | 2.92 | 3.27 |
| Ph.anh, Mal.anh, Phenol | 3.75 | 3.60 | 5.65 |
| Ph.anh, Phenol | 3.10 | 3.05 | 4.66 |
| Mal.anh, Phenol | 3.85 | 3.35 | 4.86 |
| Phenol | 2.95 | 2.70 | 4.00 |
| Ph.anh, Mal.anh, Dimethylsulfoxide | 4.51 | 4.96 | 5.23 |
| Ph.anh, Dimethylsulfoxide | 3.91 | 4.28 | 5.73 |
| Mal.anh, Dimethylsulfoxide | 3.59 | 3.30 | 4.25 |
| Dimethylsulfoxide | 3.84 | 4.22 | 3.55 |
| Ph.anh, Mal.anh, Furfural | 4.10 | 3.55 | 5.22 |
| Ph.anh, Furfural | 3.10 | 3.35 | 5.02 |
| Mal.anh, Furfural | 4.00 | 3.55 | 3.91 |
| Furfural | 3.35 | 3.25 | 4.41 |
| Ph.anh, Mal.anh, Nitrobenzene | 3.58 | 3.50 | 4.46 |
| Ph.anh, Nitrobenzene | 3.10 | 3.10 | 4.16 |
| Mal.anh, Nitrobenzene | 3.50 | 3.65 | 4.45 |
| Nitrobenzene | 2.60 | 2.95 | 3.29 |
| Ph.anh, Mal.anh, Acetophenone | 3.47 | 3.22 | 4.13 |
| Ph.anh, Acetophenone | 2.95 | 2.85 | 4.73 |
| Mal.anh, Acetophenone | 3.45 | 3.25 | 3.33 |
| Acetophenone | 2.68 | 2.53 | 2.80 |
| Ph.anh, Mal.anh, Ethylacetoacetate | 2.65 | 3.51 | 3.44 |
| Ph.anh, Ethylacetoacetate | 3.08 | 2.95 | 3.58 |
| Mal.anh, Ethylacetoacetate | 3.54 | 3.25 | 3.02 |
| Ethylacetoacetate | 2.80 | 2.46 | 2.30 |
| Ph.anh, Mal.anh, Benzophenone | 3.45 | 3.75 | 4.30 |
| Ph.anh, Benzophenone | 2.50 | 3.20 | 4.46 |
| Mal.anh, Benzophenone | 2-0 | 2.95 | 4.24 |
| Benzophenone | 2.05 | 2.42 | 3.26 |
| Ph.anh, Mal.anh, 2,4-Pentanedione | 3.50 | 3.83 | 4.90 |
| Ph.anh, 2,4-Pentanedione | 3.35 | 2.80 | 4.47 |
| Mal.anh, 2,4-Pentanedione | 3.25 | 3.20 | 3.90 |
| 2-4-Pentanedione | 2.80 | 2.52 | 3.14 |
| Ph.anh, Mal.anh, 2-Nitrotoluene | 3.45 | 3.38 | 4.05 |
| Ph.anh, 2-Nitrotoluene | 3.45 | 3.15 | 3.58 |
| Mal.anh, 2-Nitrotoluene | 3.60 | 3.15 | 4.13 |

TABLE III-continued

Relative Volatilities of Toluene to Methylcyclohexane, 2,4,4-Tri methylpentene-1 and 2,2,4-Trimethylpentane with Several Extractive Distillation Agents.

| Extractive Distillation Agent | MecycloHex-Toluene | 244TMP-1 Toluene | 224TMP Toluene |
| --- | --- | --- | --- |
| 2-Nitrotoluene | 2.55 | 2.70 | 3.50 |
| Ph.anh, Mal.anh, Sulfolane | 4.95 | 3.95 | 5.55 |
| Ph.anh, Sulfolane | 3.50 | 2-phase | 5.54 |
| Mal.anh, Sulfolane | 3.75 | 2.80 | 4.75 |
| Sulfolane | 2.25 | 1.95 | 6.31 |
| Ph.anh, Mal.anh, Triethylene glycol diacetate | 3.68 | 3.30 | 4.95 |
| Ph.anh, Triethylene glycol diacetate | 3.10 | 3.60 | 4.15 |
| Mal.anh, Triethylene glycol diacetate | 3.63 | 3.35 | 4.26 |
| Triethylene glycol diacetate | 3.10 | 2.92 | 3.27 |

Toluene is the major precursor to many processes for making explosives and dyes. In these uses it is absolutely essential that the toluene be very pure. It is the presence of impurities that make it hazardous as an explosive reagent such as trinitrotoluene or render it inconsistent as a dye intermediate. More tha half the toluene of commerce originates in or is converted from petroleum. From this source it is always accompanied by close boiling non-aromatic hydrocarbons of the paraffin, olefin and/or naphthene family.

OBJECTIVE OF THE INVENTION

The object of this invention is to provide a process or method of extractive distillation that will enhance the apparent relative volatility of toluene to close boiling non-aromatic hydrocarbons in their separation in a rectification column. It is a particular object of this invention to identify suitable mixtures of organic compounds which will increase the apparent relative volatility of toluene to close boiling non-aromatic hydrocarbons to values higher than that attained by single compounds. It is a further object of this invention to identify mixtures of organic compounds which, in addition to the above constraints, are stable, can be separated from the toluene by rectification with relatively few theoretical plates and can be recycled to the extractive distillation column and reused with little decomposition.

SUMMARY OF THE INVENTION

The objects of this invention are provided by a process for the separation of toluene from close boiling non-aromatic hydrocarbons using mixtures of phthalic anhydride, maleic anhydride and/or an oxygenated or nitrogen-containing organic compound as the agent in extractive distillation.

DETAILED ELABORATION OF THE INVENTION

I have discovered that a mixture comprising an organic compound admixed with phthalic anhydride, maleic anhydride or both, is more effective as an extractive distillation agent in the separation of toluene from close boiling non-aromatic hydrocarbons than the compound alone. In order to demonstrate this invention, I evaluated the extractive distillation agents with toluene-2,2,4-trimethylpentane, B.P.=99.2° C. (a paraffin), with toluene-2,4,4-trimethylpentene-2, B.P.=101° C. (an olefin) and with toluene-methylcyclohexane, B.P.=100.8° C. (a naphthene). These three compounds are available in high purity and boil close to toluene, B.P.=110.6° C. The relative volatility of toluene to methylcyclohexane is 1.50, to 2,4,4-trimethylpentene-2 is 1.61 and to 2,2,4-trimethylpentane is 1.79.

Table III shows the relative volatility of toluene to methylcyclohexane, 2,4,4-trimethylpentene-1 and 2,2,4-trimethylpentane with a number of solvents mixed with phthalic anhydride and maleic anhydride or both. The relative volatilities shown in Table III are the average of two runs, one at one part of extractive distillation agent per part of hydrocarbon mixture and the other at 6/5 parts of extractive distillation agent per part of hydrocarbon mixture. I have found that this is the preferred ratio of extractive distillation agent to hydrocarbon in this separation. The amount of phthalic anhydride, maleic anhydride and solvent in the ternarys shown in Table III was approximately equal to each other, as were the binarys also. The exact ratio does not appear to be critical. Likewise the relative volatilities shown in Table III does not change appreciably when the ratio of toluene to non-aromatic hydrocarbon is varied. The data presented in Table III were obtained in a glass vapor-liquid equilibrium still of the Othmer design.

THE USEFULNESS OF THE INVENTION

The usefulness or utility of this invention can be demonstrated by referring to the data presented in Tables II and III. When toluene is being separated from methylcyclohexane, relative volatility=1.50, by rectification in 99% purity, 227 plates are required at total reflux, somewhat more under a finite reflux ratio. Table III shows that a mixture of phthalic anhydride, maleic anhydride and glycerol triacetate changes the relative volatility to 4.25. From Table II it is apparent that only 63 theoretical plates will be required to effect the separation of toluene from methylcyclohexane in 99% purity. When the separation is toluene from 2,4,4-trimethylpentene-1, the improvement in relative volatility is from 1.61 to 3.45 and the theoretical plate requirement drops from 195 to 72. With 2,2,4-trimethylpentane and toluene, the relative volatility change is from 1.79 to 5.18 and the plate requirement is reduced from 160 to 56.

WORKING EXAMPLES

EXAMPLE 1

A mixture comprising 50 grams of toluene and 50 grams of methylcyclohexane was charged to an Othmer type vapor-liquid equilibrium still and the mixture refluxed for eleven hours. Samples of the vapor and liquid were removed and analysed by gas chromatography. The vapor contained 43.8% toluene, 56.2% methylcyclohexane, the liquid 54.1% toluene, 45.9% methylcyclohexane. This indicates a relative volatility of methylcyclohexane to toluene of 1.50. This has been confirmed by other investigators.

EXAMPLE 2

A mixture comprising 50 grams of toluene and 50 grams of 2,4,4-trimethylpentene-1 was charged to the Othmer vapor-liquid equilibrium still and refluxed for seven hours. Samples of the vapor and liquid were removed and analysed. The vapor contained 58% 2,4,4-trimethylpentene-1, 42% toluene, the liquid 46.2% 2,4,4-trimethylpentene-1 and 54.8% toluene. This indicates a relative volatility of 1.61.

EXAMPLE 3

A mixture comprising 50 grams of toluene and 50 grams of 2,2,4-trimethylpentane was charged to the Othmer vapor-liquid equilibrium still and refluxed for twelve hours. The vapor contained 59.3% 2,2,4-trimethylpentane and 40.7% toluene, the liquid 44.8% 2,2,4-trimethylpentane and 55.2% toluene. This indicates a relative volatility of 1.79.

EXAMPLE 4

A mixture comprising 25 grams of methylcyclohexane, 25 grams of toluene and 50 grams of glycerol triacetate was charged to the vapor-liquid equilibrium still and refluxed for twelve hours. Analyses indicated a vapor composition of 63.9% methylcyclohexane, 36.1% toluene and a liquid composition of 38.2% methylcyclohexane, 61.8% toluene. This indicates a relative volatility of 2.86. Ten grams of glycerol triacetate was added and refluxing continued for another twelve hours. Analyses then gave a vapor composition of 63.7% methylcyclohexane, 36.3% toluene and a liquid composition of 38.2% methylcyclohexane, 61.8% toluene which indicates a relative volatility of 2.83.

EXAMPLE 5

A mixture comprising 25 grams of 2,4,4-trimethylpentene-1, 25 grams of toluene and 50 grams of glycerol triacetate was charged to the vapor-liquid equilibrium still and refluxed for twelve hours. Analyses indicated a vapor composition of 60.1% 2,4,4-trimethylpentene-1, 39.9% toluene and a liquid composition of 35.2% 2,4,4-trimethylpentene-1, 64.8% toluene. This indicates a relative volatility of 2.77. Ten grams of glycerol triacetate was added and refluxing continued for another eleven hours. Analyses then gave a vapor composition of 59.2% 2,4,4-trimethylpentene-1, 40.8% toluene and a liquid composition of 34.1% 2,4,4-trimethylpentene-1, 65.9% toluene which indicates a relative volatility of 2.81.

EXAMPLE 6

A mixture comprising 25 grams of 2,2,4-trimethylpentane, 25 grams of toluene and 50 grams of glycerol triacetate was charged to the vapor-liquid equilibrium still and refluxed for twelve hours. Analyses indicated a vapor composition of 63.6% 2,2,4-trimethylpentane, 36.4% toluene and a liquid composition of 57.7% 2,2,4-trimethylpentane, 42.3% toluene. This indicates a relative volatility of 3.29. Ten grams of glycerol triacetate was added and refluxing continued for another eight hours. Analyses then gave a vapor composition of 59.8% 2,2,4-trimethylpentane, 40.2% toluene and a liquid composition of 35.2% 2,2,4-trimethylpentane, 64.8% toluene which indicates a relative volatility of 2.73.

EXAMPLE 7

A mixture comprising 25 grams of methylcyclohexane, 25 grams of toluene, 25 grams of maleic anhydride and 25 grams of glycerol triacetate was charged to the vapor-liquid equilibrium still and refluxed for thirteen hours. Analyses indicates a vapor composition of 49.2% methylcyclohexane, 50.8% toluene and a liquid composition of 22.7% methylcyclohexane, 77.3% toluene. This indicates a relative volatility of 3.30. Five grams of maleic anhydride and five grams of glycerol triacetate were added and refluxing continued for another nine hours. Analyses then gave a vapor composition of 30% methylcyclohexane, 70% toluene and a liquid composition of 12.9% methylcyclohexane, 87.1% toluene which indicates a relative volatility of 2.90.

EXAMPLE 8

A mixture comprising 25 grams of 2,4,4-trimethylpentene-1, 25 grams of toluene, 25 grams of maleic anhydride and 25 grams of glycerol triacetate was charged to the vapor-liquid equilibrium still and refluxed for ten hours. Analyses indicated a vapor composition of 54.6% 2,4,4-trimethylpentene-1, 45.4% toluene and a liquid composition of 23.1% 2,4,4-trimethylpentene-1, 76.9% toluene which indicates a relative volatility of 4.01. Five grams of maleic anhydride and five grams of glycerol triacetate were added and refluxing continued for another twelve hours. Analyses then gave a vapor composition of 44.3% 2,4,4-trimethylpentene-1, 55.7% toluene and a liquid composition of 19.4% 2,4,4-trimethylpentene-1, 80.6% toluene which indicates a relative volatility of 3.31.

EXAMPLE 9

A mixture comprising 25 grams of 2,2,4-trimethylpentane, 25 grams of toluene, 25 grams of maleic anhydride and 25 grams of glycerol triacetate was charged to the vapor-liquid equilibrium still and refluxed for fifteen hours. Analyses indicated a vapor composition of 54.9% 2,2,4-trimethylpentane, 45.1% toluene and a liquid composition of 22.7% 2,2,4-trimethylpentane, 77.3% toluene which indicates a relative volatility of 4.15. Five grams of maleic anhydride and five grams of glycerol triacetate was added and refluxing continued for another six hours. Analyses then gave a vapor composition of 54.4% 2,2,4-trimethylpentane, 45.6% toluene and a liquid composition of 22.4% 2,2,4-trimethylpentane, 77.6% toluene which indicates a relative volatility of 4.13.

EXAMPLE 10

A mixture comprising 25 grams of methylcyclohexane, 25 grams of toluene, 25 grams of phthalic anhydride and 25 grams of glycerol triacetate was charged to the vapor-liquid equilibrium still and refluxed for twelve hours. Analyses indicated a vapor composition of 64.8% methylcyclohexane, 35.2% toluene and a liquid composition of 36.8% methylcyclohexane, 63.2% toluene which indicates a relative volatility of 3.16. Five grams of phthalic anhydride and five grams of glycerol triacetate were added and refluxing continued for another fourteen hours. Analyses then gave a vapor composition of 64.9% methylcyclohexane, 35.1% toluene and a vapor composition of 36.4% methylcyclohexane, 63.6% toluene which indicates a relative volatility of 3.24.

EXAMPLE 11

A mixture comprising 25 grams of 2,4,4-trimethylpentene-1, 25 grams of toluene, 25 grams of phthalic anhydride and 25 grams of glycerol triacetate was charged to the vapor-liquid equilibrium still and refluxed for thirteen hours. Analyses indicated a vapor composition of 60% 2,4,4-trimethylpentene-1, 40% toluene and a liquid composition of 31.5% 2,4,4-trimethylpentene-1, 68.5% toluene which indicates a relative volatility of 3.26. Five grams of phthalic anhydride and five of glycerol triacetate were added and refluxing continued for another ten hours. Analyses then gave a vapor composition of 61.6% 2,4,4-trimethylpentene-1, 38.4% toluene and a liquid composition of 30.3% 2,4,4-trimethylpentene-1, 69.7% toluene which indicates a relative volatility of 3.68.

EXAMPLE 12

A mixture comprising 25 grams of 2,2,4-trimethylpentane, 25 grams of toluene, 25 grams of phthalic anhydride and 25 grams of glycerol triacetate was charged to the vapor-liquid equilibrium still and refluxed for fifteen hours. Analyses indicated a vapor composition of 61.5% 2,2,4-trimethylpentane, 38.5% toluene and a liquid composition of of 29.6% 2,2,4-trimethylpentane, 70.4% toluene which indicates a relative volatility of 3.81. Five grams of phthalic anhydride and five grams of glycerol triacetate were added and refluxing continued for another six hours. Analyses then gave a vapor composition of 63% 2,2,4-trimethylpentane, 37% toluene and a liquid composition of 28.6% 2,2,4-trimethylpentane, 71.4% toluene which indicates a relative volatility of 4.25.

EXAMPLE 13

A mixture comprising 25 grams of methylcyclohexane, 25 grams of toluene, 17 grams of phthalic anhydride, 17 grams of maleic anhydride and 17 grams of glycerol triacetate was charged to the vapor-liquid equilibrium still and refluxed for nine hours. Analyses indicated a vapor composition of 55.3% methylcyclohexane, 44.7% toluene and a liquid conposition of 22.4% methylcyclohexane, 77.6% toluene which indicates a relative volatility of 4.28. Three grams of phthalic anhydride, three grams of maleic anhydride and three grams of glycerol triacetate were added and refluxing continued for another eleven hours. Analyses then gave a vapor composition of 53.8% methylcyclohexane, 46.2% toluene and a liquid composition of 21.7% methylcyclohexane, 78.3% toluene which indicates a relative volatility of 4.21.

EXAMPLE 14

A mixture comprising 25 grams of 2,4,4-trimethylpentene-1, 25 grams of toluene, 17 grams of phthalic anhydride, 17 grams of maleic anhydride and 17 grams of glycerol triacetate was charged to the vapor-liquid equilibrium still and refuxed for twelve hours. Analyses indicated a vapor composition of 57.2% 2,4,4-trimethylpentene-1, 42.8% toluene and a liquid composition of 28.2% 2,4,4-trimethylpentene-1, 61.8% toluene which indicates a relative volatility of 3.41. Three grams of phthalic anhydride, three grams of maleic anhydride and three grams of glycerol triacetate were added and refluxing continued for another fourteen hours. Analyses then gave a vapor composition of 53.5% 2,4,4-trimethylpentene-1, 46.5% toluene and a liquid composition of 24.7% 2,4,4-trimethylpentene-1, 75.3% toluene which indicates a relative volatility of 3.50.

EXAMPLE 15

A mixture comprising 25 grams of 2,2,4-trimethylpentane, 25 grams of toluene, 17 grams of phthalic anhydride, 17 grams of maleic anhydride and 17 grams of glycerol triacetate was charged to the vapor-liquid equilibrium still and refluxed for five hours. Analyses indicated a vapor composition of 61.2% 2,2,4-trimethylpentane, 38.8% toluene and a liquid composition of 23.4% 2,2,4-trimethylpentane, 76.6% toluene which indicates a relative volatility of 5.15. Three grams of phthalic anhydride, three grams of maleic anhydride and three grams of glycerol triacetate were added refluxing continued for another six hours. Analyses then gave a vapor composition of 57.8% 2,2,4-trimethylpentane, 42.2% toluene and a liquid composition of 20.8% 2,2,4-trimethylpentane, 79.2% toluene which indicates a relative volatility of 5.21.

The above examples serve to show in detail how the data presented in Table III was obtained. Each of the solvent combinations reported there was determined in this manner.

EXAMPLE 16

A column consisting of one ten plate section of one-inch diameter glass perforated plates equipped with a vacuum jacket was employed. The column was fitted with a Corad constant reflux ratio distilling head. Between the Corad head and the top of the column, a feed line from a constant flow bellows pump was introduced. The column had been calibrated with a test mixture of ethylbenzene and p-xylene, which mixture possesses a relative volatility of 1.06. The column calibrated 4.5 theoretical plates at total reflux. A run was made with a charge comprising approximately 10% methylcyclohexane, 90% toluene in the stillpot. The column was operated at total reflux for about an hour and then the pump started at a rate to deliver about one part of extractive agent to one part of methylcyclohexane-toluene being boiled up. The extractive agent in this example was 33.3% phthalic anhydride, 33.3% maleic anhydride and 33.3% glycerol triacetate. The following data were obtained:

| Time, hours | Overhead Composition, % MCH | % Tol. | Stillpot Composition, % MCH | % Tol. | Relative Volatility |
|---|---|---|---|---|---|
| 1 | 88.7 | 11.3 | 6.4 | 93.6 | 2.87 |
| 2 | 97.0 | 3.0 | 5.3 | 94.7 | 4.11 |
| 3 | 97.8 | 2.2 | 4.9 | 95.1 | 4.48 |

It will be noted that after about two hours, equilibrium has been achieved and the relative volatility remains essentially constant in the range 4.1 to 4.5. Without the extractive agent it would have been 1.50.

I have shown by experimental data and examples that the proper combination of phthalic anhydride and/or maleic anhydride with a suitable solvent will yield separations of toluene from close boiling naphthenes, olefins or paraffins that are far better than what is obtainable by any of these compounds individually. The total effect of the mixture far exceeds the sum of the parts.

The nature of the present invention having been described and illustrated by examples, what I wish to claim as new and useful and secure by Letters Patent is:

1. A method for separating toluene from close boiling non-aromatic hydrocarbons which comprises distilling a mixture of toluene and close boiling non-aromatic hydrocarbons in a rectification column in the presence of an effective amount of an extractive agent sufficient to provide a relative volatility of 2.5 or greater comprising effective proportions of phthalic anhydride and/or maleic anhydride and a solvent from the group consisting of glycerol triacetate, dimethylformamide, ethyl acetoacetate, acetonyl acetone, acetophenone, 2,4-pentanedione, ethylene glycol phenyl ether, dichlorodiethyl ether, dimethylacetamide, benzophenone, ethylene glycol diacetate, furfural, nitrobenzene, 2-nitrotoluene, sulfolane, phenol, dimethylsulfoxide.

2. The method of claim 1 in which the extractive agent is phthalic anhydride and a solvent from the group listed in claim 1.

3. The method of claim 1 in which the extractive agent is maleic anhydride and a solvent from the group listed in claim 1.

* * * * *